United States Patent
Uzunbajakava et al.

(10) Patent No.: US 8,417,323 B2
(45) Date of Patent: Apr. 9, 2013

(54) APPARATUS FOR DEPTH-RESOLVED MEASUREMENTS OF PROPERTIES OF TISSUE

(75) Inventors: Natallia Uzunbajakava, Eindhoven (NL); Rachel Estelle Thilwind, Eindhoven (NL); Joachim Kahlert, Aachen (DE); Gerhardus Wilhelmus Lucassen, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/302,053

(22) PCT Filed: May 30, 2007

(86) PCT No.: PCT/IB2007/052026
§ 371 (c)(1),
(2), (4) Date: Nov. 24, 2008

(87) PCT Pub. No.: WO2007/138552
PCT Pub. Date: Dec. 6, 2007

(65) Prior Publication Data
US 2009/0143774 A1    Jun. 4, 2009

(30) Foreign Application Priority Data
May 30, 2006  (EP) .................................. 06114718

(51) Int. Cl.
*A61B 6/00* (2006.01)
(52) U.S. Cl. .................. 600/478; 600/473; 600/476
(58) Field of Classification Search ........... 600/473–480
See application file for complete search history.

(56) References Cited

U.S. PATENT DOCUMENTS

| | | | | |
|---|---|---|---|---|
| 5,192,278 A * | 3/1993 | Hayes et al. | ..................... | 606/15 |
| 5,197,470 A | 3/1993 | Helfer et al. | | |
| 5,496,305 A * | 3/1996 | Kittrell et al. | ................... | 606/15 |
| 6,144,791 A * | 11/2000 | Wach et al. | ..................... | 385/123 |
| 6,286,514 B1 * | 9/2001 | Lemelson | ..................... | 128/899 |
| 6,701,181 B2 * | 3/2004 | Tang et al. | ..................... | 600/478 |
| 6,711,426 B2 * | 3/2004 | Benaron et al. | ............... | 600/342 |
| 6,816,743 B2 * | 11/2004 | Moreno et al. | ............... | 600/473 |
| 7,426,410 B2 * | 9/2008 | Zuluaga et al. | ............... | 600/476 |

(Continued)

FOREIGN PATENT DOCUMENTS

| WO | 9303672 A1 | 3/1993 |
|---|---|---|
| WO | 0150955 A1 | 7/2001 |
| WO | 2006045013 A2 | 4/2006 |

OTHER PUBLICATIONS

H. Martens, et al: Multivariate Calibration 1 edition Jul. 28, 1992.
D. J. Segelstein, "The complex reflective index of water", University of Missouri-Kansas City (1981).
W. B. Grather: Med. Res. Council Labs, Holly Hill, London and N. Kollias, Wellman Laboratories, Harvard Medical School, Boston, 1960.

(Continued)

*Primary Examiner* — Sanjay Cattungal

(57) ABSTRACT

An apparatus for depth-resolved measurements of properties of tissue includes an illuminator that illuminates the tissue with light, a collector for collecting light which has not been absorbed by the tissue, and a determination device configured to determine properties of the tissue in different depths from the collected light. A casing for advancing into a hollow object includes at least a part of the illuminator and collector. The illuminator and collector are configured to collect light depth-resolved, and the determination device is configured to determine depth-resolved properties of the tissue from the light which has been collected depth-resolved.

23 Claims, 15 Drawing Sheets

U.S. PATENT DOCUMENTS

Figure 1:
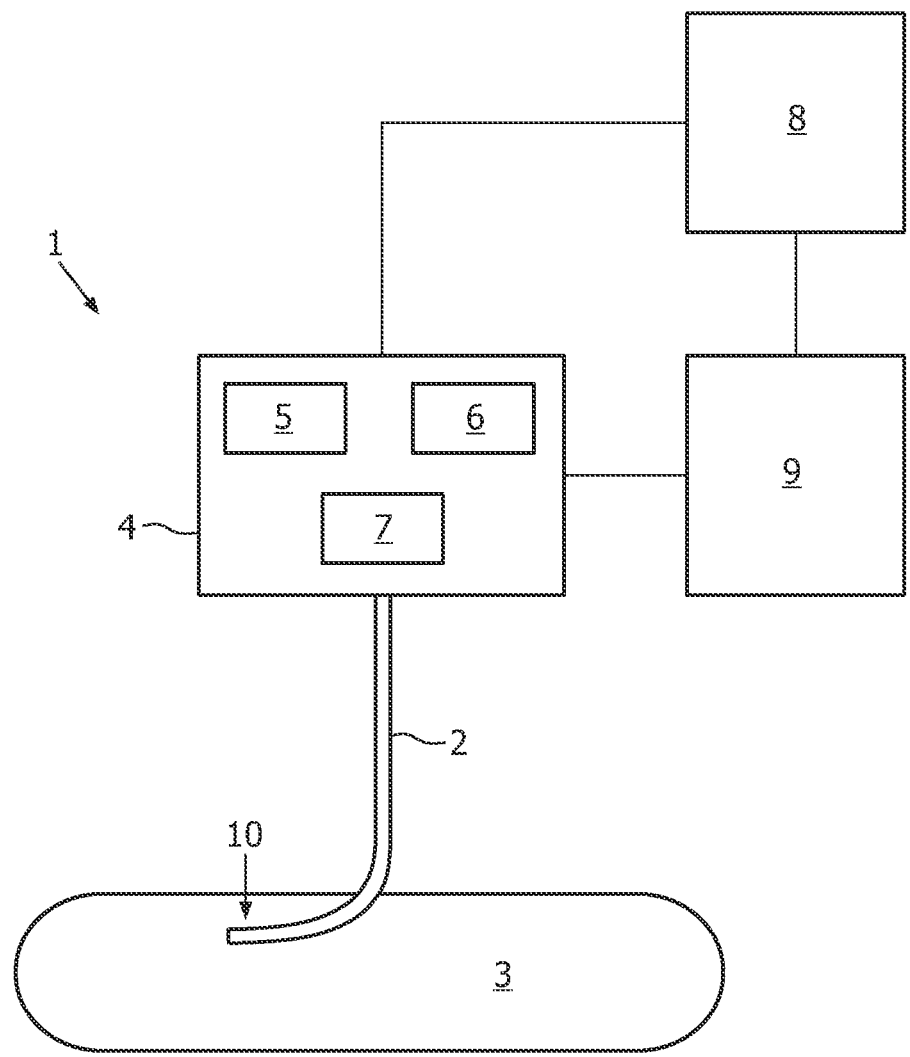

| | | | |
|---|---|---|---|
| 7,486,985 B2* | 2/2009 | Marshik-Geurts et al. | 600/473 |
| 7,668,587 B2* | 2/2010 | Benaron et al. | 600/476 |
| 7,865,231 B2* | 1/2011 | Tearney et al. | 600/476 |
| 7,996,069 B2* | 8/2011 | Zuluaga et al. | 600/476 |
| 2002/0045811 A1* | 4/2002 | Kittrell et al. | 600/407 |
| 2004/0024321 A1* | 2/2004 | Marshik-Geurts et al. | 600/473 |
| 2004/0077950 A1* | 4/2004 | Marshik-Geurts et al. | 600/475 |
| 2004/0249289 A1* | 12/2004 | Zuluaga et al. | 600/473 |
| 2005/0159646 A1 | 7/2005 | Nordstrom et al. | |
| 2005/0251116 A1* | 11/2005 | Steinke et al. | 606/8 |
| 2005/0267340 A1* | 12/2005 | Ishihara et al. | 600/310 |
| 2006/0184037 A1* | 8/2006 | Ince et al. | 600/476 |
| 2008/0188727 A1* | 8/2008 | Benaron et al. | 600/323 |
| 2008/0221455 A1* | 9/2008 | Marshik-Geurts et al. | 600/473 |
| 2009/0012407 A1* | 1/2009 | Zuluaga et al. | 600/478 |
| 2011/0092823 A1* | 4/2011 | Tearney et al. | 600/476 |

OTHER PUBLICATIONS

Janda et al: "Comparison of thermal tissue effects induced by contact applications of fiber guided laser systems", Lasers in surgery and medicine, vol. 33, pp. 93-101 2003.

Splinter et al: "Optical properties of normal, diseased, and laser photocoagulated myocardium at the Nd:YAG wavelength", Lasers in surgery and medicine, vol. 11, pp. 117-124 (1991).

Everett, et al: "Birefringence characterization of biological tissue by use of optical coherence tomography", Optics Letters, 23/3:228-230 (1998).

Lin et al: "Dynamics of tissue optics during laser heating of turbid media", Applied Optics, 35/19:34133420 (1996).

\* cited by examiner

APPARATUS FOR DEPTH-RESOLVED MEASUREMENTS OF PROPERTIES OF TISSUE

The invention relates to an apparatus and a method for depth-resolved measurements of properties of tissue. The invention relates further to an ablation apparatus for ablating tissue comprising the apparatus for depth-resolved measurements of properties of tissue.

The depth-resolved measurement of properties of tissue is particularly important in the field of cardiac ablation, wherein the tissue is human tissue, i.e., the properties of human tissue have to be determined. Cardiac ablation is used to treat abnormally rapid heartbeats that cannot be controlled with medication, or in patients that cannot tolerate these medications. During this therapy a cardiac ablation catheter is inserted into the heart via a blood vessel. The catheter is navigated by images created by fluoroscopy and/or other imaging modalities. Generally, radiofrequency (RF) energy or intense cold (cryoablation) are used to thermally damage a small volume of tissue. The damaged tissue acts as an electrical isolator, blocking abnormal signals that over-stimulate the heart.

Also laser light can be used to heat up the tissue and induce damage. The laser-based treatment using selected wavelengths provides increased depth of penetration and a greater control over lesion size and shape compared with cardiac ablation systems which use radiofrequency energy or intense cold. Moreover, a laser-based system is compatible with magnetic resonance imaging (MRI) systems.

The measured depth-resolved properties of the tissue can be used to control the ablation procedure, for instance, the necessary laser power and/or the duration of the treatment.

The depth-resolved determination of properties of tissue is also important to distinguish diseased from healthy tissue.

The U.S. Pat. No. 5,197,470 discloses an instrument which illuminates tissue with near-infrared radiation and determines from the absorption spectra of the light which has not been absorbed by the tissue, whether the tissue is diseased or not. But in the case, in which the diseased tissue is covered by healthy tissue, this instrument cannot determine the depth in which diseased tissue is located making the ablation treatment quite difficult.

It is therefore an object of the invention to provide an apparatus for depth-resolved measurements of properties of tissue, which can determine the properties of the tissue in different depths, in particular, which can determine the depth position of diseased tissue, even if the diseased tissue is covered by healthy tissue, and which can in particular determine the properties of inside tissue of a hollow object.

This object is achieved by an apparatus for depth-resolved measurements of properties of tissue, said apparatus comprising:
a) illumination means which is adapted to illuminate the tissue with light,
b) collector means for collecting light which has not been absorbed by the tissue,
c) determination means for determining properties of the tissue in different depths from the collected light,
d) a casing, in which at least a part of the illumination means and the collector means are located, for advancing into a hollow object,
wherein the illumination means and the collector means are adapted to collect light depth-resolved, and wherein the determination means is adapted to determine depth-resolved properties of the tissue from the light, which has been collected depth-resolved.

The casing can be flexible or rigid and is, for example, a catheter or an endoscope.

The tissues is, for example, inside tissue of a hollow object.

Since the light is collected depth-resolved, i.e. light signals are collected such that they can be separated depending on their penetration depth in the tissue, to each light signal a penetration depth can be assigned and the determination means can determine the properties of the object, i.e. the tissue, in different depths by using the light signals to which different penetration depths have been assigned. Since at least a part of the illumination means and the collector means are located within a casing for advancing into a hollow object, at least a part of the illumination means and of the collector means can be advanced into a hollow object to a location of tissue, which, for example, has to be treated, and the tissue can be illuminated by the illumination means and the light, which has not been absorbed by the tissue, can be collected depth-resolved.

According to an embodiment of the invention, the illumination means and the collector means are adapted to collect light signals of the light which has not been absorbed by the tissue, wherein at least some of the light signals have penetrated the tissue up to different penetration depths, and wherein the determination means is adapted to determine the properties of the tissue in different depths from the light signals. Since the collected light signals have penetrated the tissue up to different penetration depths, the determination unit can determine from the light signals the properties of the tissue in different depths.

The illumination means and the collector means can be adapted to collect light signals of the light which has been directly reflected at the surface of the object to determine the properties also at the surface of the tissue.

In order to determine depth-resolved properties from the collected light, the apparatus for depth-resolved measurements of properties of tissue can comprise a detector, which converts the light signals into electronic detection signals. The detection signals can be transferred to the determination unit, which is preferentially a determination computer and which determines properties of tissue in different depths from the detection signals, i.e. from the collected light.

The illumination means and the collector means can be adapted to collect light signals which have entered the tissue at an entering position and which have left the tissue at a leaving position, wherein for at least some of the collected light signals the distance between the entering position and the leaving position is different. Since the penetration depth is larger for a light signal whose entering position and leaving position have a larger distance from each other than the penetration depth for a light signal whose entering position and leaving position have a smaller distance and since the relation between the distance of the entering position and the leaving position and the penetration depth is known or can be determined by calibration, to each distance of entering position and leaving position, i.e. to each light signal, a penetration depth can be assigned, and the determination unit can determine the properties of the tissue in different depths from the light signals and the assigned penetration depths.

In particular, the illumination means can comprise an illuminator and the collector means can comprise collectors, wherein each collector is located at a predetermined distance from a position at which the illuminator is located and wherein the predetermined distances from at least two collectors are different, i.e. the illuminator is located at the entering position and the collectors are located at different leaving positions, wherein the distance between the entering position and a leaving position at which a collector is located is different from the distance between the entering position and at least one other leaving position at which another collector is located. By using this arrangement, the tissue is illuminated by light from the illuminator, and the light is partially absorbed, scattered and/or reflected in the tissue. Light, which has not been absorbed, is collected by the collectors, wherein light, which has been collected by one collector having a certain distance to the illuminator, comprises another penetration depth than light, which has been collected by another collector having a distance to the illuminator which is different from the certain distance. Thus, light collected by a certain collector corresponds to a certain penetration depth allowing to collect light depth-resolved. The depth-resolved measured light is used to determine properties of the tissue depth-resolved.

In another embodiment according to the invention, the illumination means can comprise illuminators and the collector means can comprise a collector, wherein each illuminator is located at a predetermined distance from a position at which the collector is located and wherein the predetermined distances from at least two illuminators are different. In this embodiment the tissue is illuminated by light from different illuminators, wherein at least some of these illuminators illuminate the tissue at different positions, i.e. at different entering positions. As mentioned above, the light is partially absorbed, scattered and/or reflected in the tissue, wherein light, which has not been absorbed, is collected by the collector. Light, which is emanated from one illuminator having a certain distance to the collector, comprises another penetration depth than light, which is emanated from another illuminator having a distance to the collector which is different from the certain distance. Thus, light emanated from a certain illuminator and which has been collected by the collector corresponds to a certain penetration depth allowing to collect light depth-resolved. Also this depth-resolved measured light can be used to determine properties of the tissue depth-resolved.

In an embodiment according to the invention, the illumination means comprises an illuminator and the collector means comprises a collector, wherein the illuminator is adapted to illuminate the tissue with light having different wavelengths and wherein the collector is adapted to collect the light having different wavelengths which has not been absorbed by the tissue, and wherein the determination means is adapted to assign to each of the different wavelengths a penetration depth and to determine from light with a wavelength the properties of the tissue at the penetration depth which has been assigned to the respective wavelength. Since light of different wavelengths comprise different penetration depths and since the light is collected such that the different wavelengths can be separated from each other, the light is collected depth-resolved. Furthermore, since the determination means assigns to different wavelengths different penetration depths, the determination means can efficiently determine the properties in different depths of the tissue.

According to another embodiment of the invention, the illumination means and the collector means are adapted to be moveable relatively to each other in order to collect light signals having different penetration depths, i.e. the distance between the entering position and the leaving position can be modified. The illumination means and the collector means are moveable relatively to each other, if, for instance, the illumination means is fixed relative to the apparatus and the collector means is moveable relative to the illumination means. Then, the illumination means illuminates the object with light and the non-absorbed light can be collected by the collector means at different collector positions, i.e. at different leaving positions. The distance between the illumination means and the collector means relates to a penetration depth. Thus, by collecting light at different collector positions the light is collected depth-resolved in an effective way.

It is preferred that
a) the illumination means comprises several illuminators, wherein the collector means comprises at least one collector and wherein at least two of the illuminators are positioned at the same distance with respect to at least one collector, or
b) the illumination means comprises at least one illuminator, wherein the collector means comprises several collectors and wherein at least two of the collectors are positioned at the same distance with respect to at least one collector.

For instance, the illumination means can comprise multiple illumination fibers and the collector means can comprise one collector fiber or one collector fiber bundle, wherein the multiple illumination fibers form a ring, i.e., are positioned equidistantly, or a spiral, i.e., are positioned at the different distances around the collector fiber or the collector fiber bundle. The illumination fibers can be moveable with respect to the collector fiber or the collector fiber bundle, i.e., the radius of the ring can vary with time. Alternatively, the collector means can comprise multiple collector fibers and the illumination means can comprise one illumination fiber or one illumination fiber bundle, wherein the multiple collector fibers form a ring around the illumination fiber or the illumination fiber bundle. The collector fibers can be moveable with respect to the illumination fiber or the illumination fiber bundle, i.e., the radius of the ring can vary with time. In a further embodiment, the illumination means can comprise a circular aperture of a variable diameter and a collector means, or the collector means can comprise a circular aperture of a variable diameter and an illumination means, to collect light which has penetrated the object up to different penetration lengths.

If multiple illumination sources, e.g., multiple fibers positioned at the same distance with respect to the detection means, or a ring are used, the amount of light launched into the tissue is larger. This increases the amount of the detected signal. The same is true for multiple collection means.

It is preferred that the illumination or detection means is a ring of a variable diameter or a set of fibers arranged in a spiral with respect to the detection or illumination fiber, respectively. Also by using this arrangement, the amount of the detected light becomes larger.

The illumination means and/or the collector means comprise preferably a microprism and/or a microlens and/or a micromirror and/or an optical fiber and/or a waveguide to minimize the size of the illumination means and the collector means of the apparatus according to the invention allowing to introduce the illumination means and the collector means in the casing.

It is further preferred that the detected signal is spectrally decomposed into a spectrum using a dispersion element, such as diffraction grating or a prism. This allows determining properties of tissue, which correspond to certain wavelengths or wavelength ranges, in an efficient way.

The illumination means can comprise a grating coupler to couple the light into the tissue which allows a simple coupling of light into the tissue.

It is preferred that the apparatus for depth-resolved measurements of properties of tissue comprises one or multiple (linear array or a 2D array) Si or InGaAs detectors to detect the signal. The use of these detectors yield good quality detection signals improving the quality of the measurement of properties of the tissue.

It is preferred that the apparatus is adapted to use
a) near-infrared light and/or
b) visible light and/or
c) wavelengths, which correspond to absorption bands of heme-containing proteins, water and proteins, and/or
d) wavelengths within a band around 414 nm, 434 nm, 542 nm, 556 nm, 576 nm, 758 nm, 914 nm, 1200 nm, 1439 nm and/or 1932 nm, and/or
e) wavelengths between 1600 and 1900 nm.

Light comprising these wavelengths penetrates into human tissue, which is the preferred tissue, up to a depth of some millimetres depending on the wavelength. Furthermore, these wavelengths are preferred, since spectra comprising these wavelengths are sensitive to changes of human tissue. Thus, by using these wavelengths changes, in particular, of human tissue, for example, of heart tissue, can reliably be detected and determined.

It is further preferred that the illumination means and/or the collector means comprise one or more polarizing components, for example, polarizers, in order to detect changes in the polarization of the light induced by the tissue. Thus, properties of the tissue can be determined by detecting these polarization changes.

It is further preferred that the casing is a catheter.

With this catheter, if inserted into a human body, e.g. in a blood vessel, properties of the tissue inside the human body can be determined depth-resolved. This is particularly useful in connection with a treatment of the tissue, so that changes caused by the treatment can be observed, or that it can be determined which part of the tissue has to be treated or how the treatment progresses.

It is further preferred that the illumination means and the collector means comprise a microprism and/or a microlens and/or a micromirror and/or an optical fiber and/or a waveguide, which are located inside the catheter to miniaturize the illumination means and the collector means and thus the catheter to simplify the insertion of the catheter.

The casing, which is, in particular, a catheter, can comprise an optical window which is transparent at least for a predetermined range of wavelengths or at least for a predetermined wavelength of light with which the tissue is to be illuminated. This optical window protects the collector means and illumination means for particles like blood cells. In particular, this optical window is coated with a substance which is adapted to prevent agglomeration of particles on the optical window. In particular, this substance is an organic substance.

It is a further object of the invention to provide a laser ablation apparatus, which can determine the properties of tissue in different depths, in particular, which can determine the depth position of diseased tissue which is covered by healthy tissue and which can determine the progress of the treatment.

This object is achieved by a laser ablation apparatus where the properties of tissue can be determined depth-resolved before, during or after an ablation procedure. Since the properties can be determined depth-resolved the progress of the treatment and the depth position of diseased tissue can be determined, even if the diseased tissue is covered by healthy tissue. This allows to perform the ablation procedure adapted to the progress of the treatment and/or to the depth-position of the diseased tissue, e.g. the laser power and/or the ablation duration can be adapted to the progress of the treatment and/or to the depth-position of the diseased tissue.

It is a further object of the invention to provide a method which can be used to determine the properties of tissue in different depths. This object is achieved by a method for depth-resolved measurements of properties of tissue comprising following steps:
a) advancing illumination means and collector means of an apparatus for depth-resolved measurements of properties of tissue into a hollow object,
b) illuminating the tissue with light by the illumination means,
c) collecting light, which has not been absorbed by the tissue, by the collector means,
d) determining properties of the tissue in different depths from the collected light by determination means,
wherein the light is collected depth-resolved and wherein depth-resolved properties of the tissue are determined from the light, which has been collected depth-resolved.

As mentioned above, since the light is collected depth-resolved, i.e. light signals are collected such that they can be separated depending on their penetration depth in the tissue, to each light signal a penetration depth can be assigned and the determination means can determine the properties of the tissue in different depths by using the light signals to which different penetration depths have been assigned.

It is preferred that the depth-resolved measurements of properties of tissue are determined by using multivariate analysis. The use of a multivariate analysis allows to determine the properties of the tissue in an efficient way, in particular, if tissue spectra have to be analysed.

Figure 2:
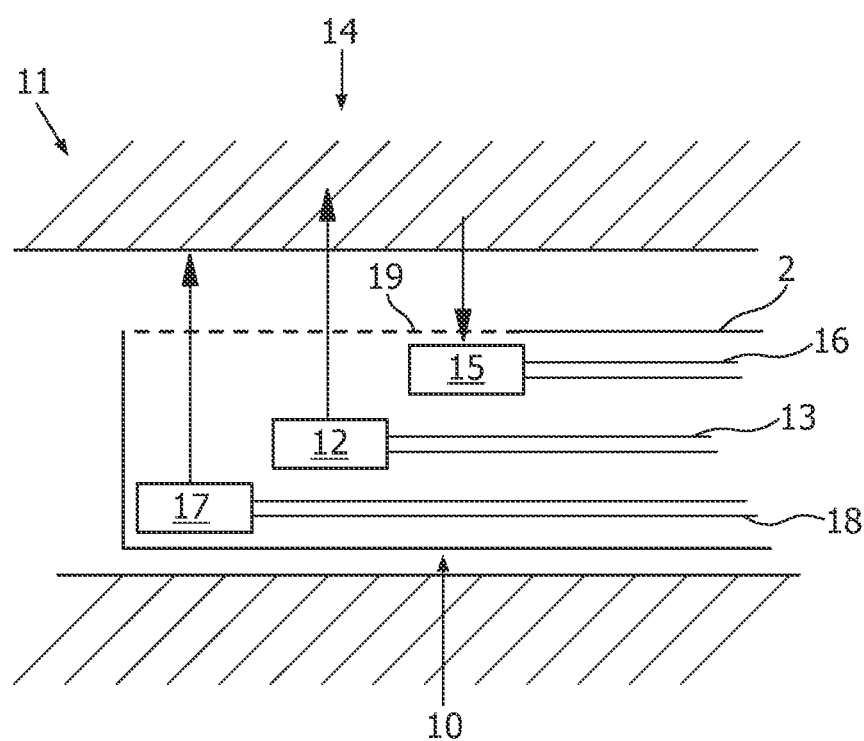
Figure 3:
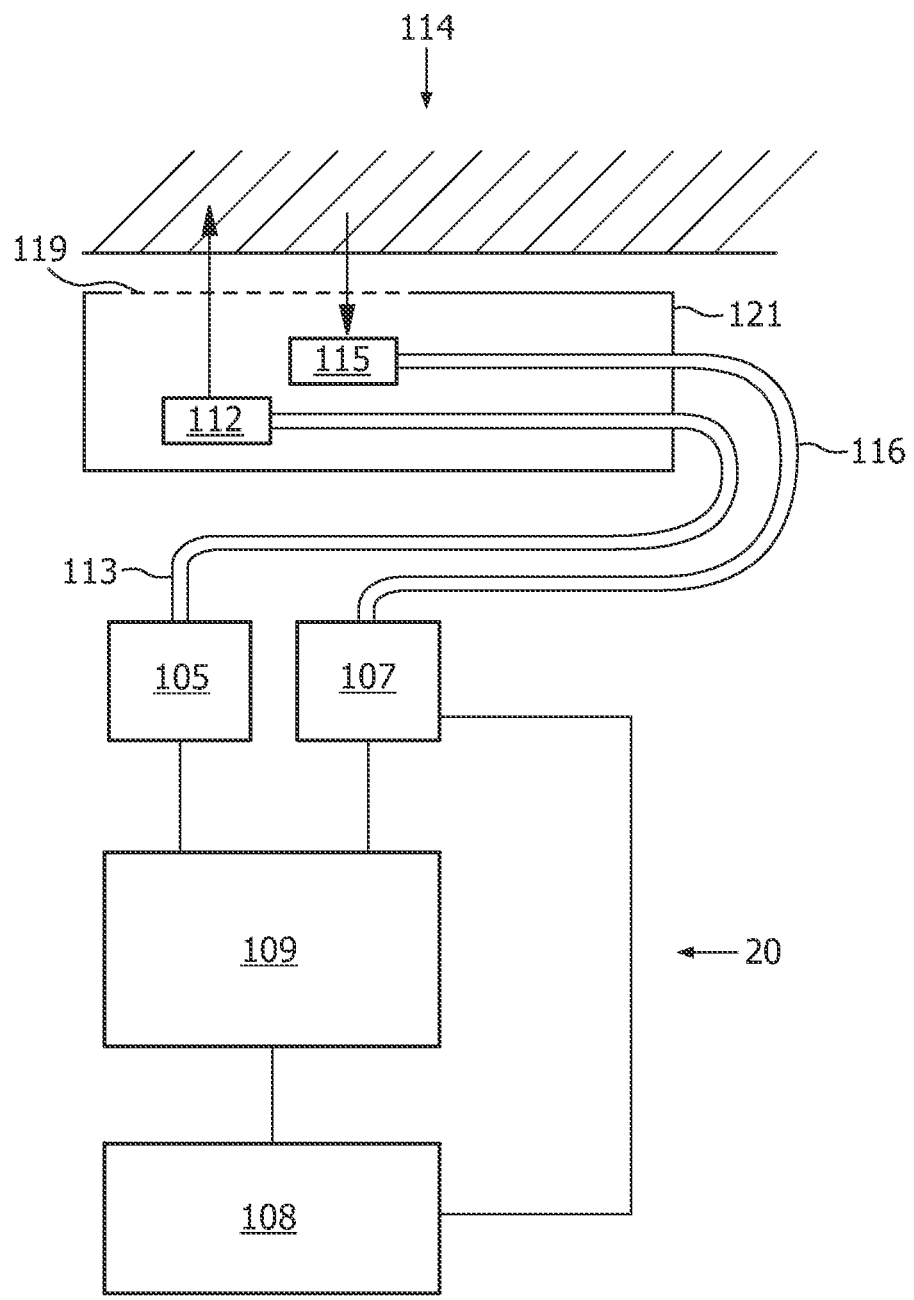
Figure 4:
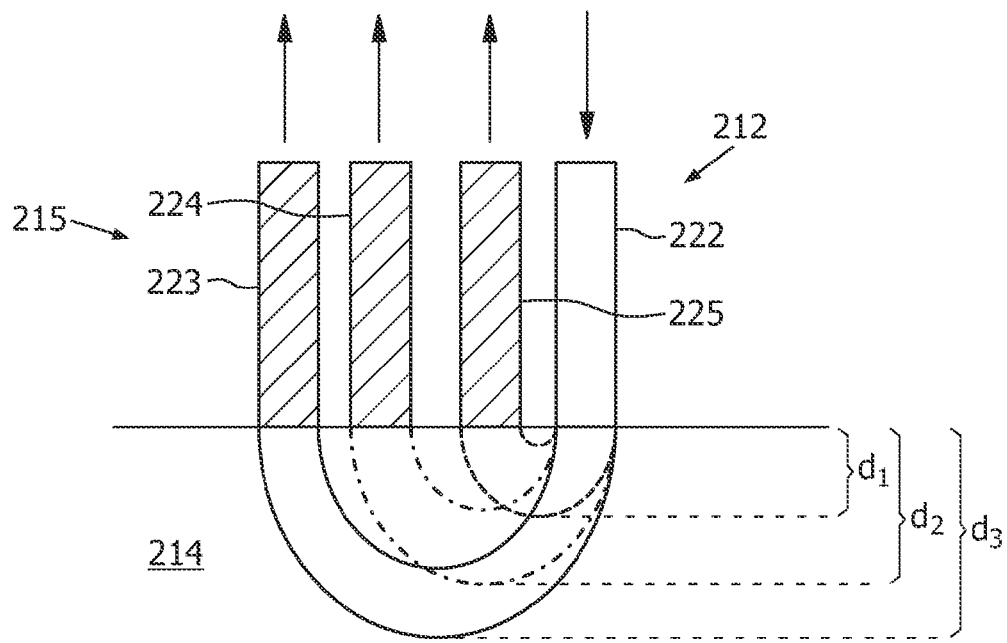
Figure 5:
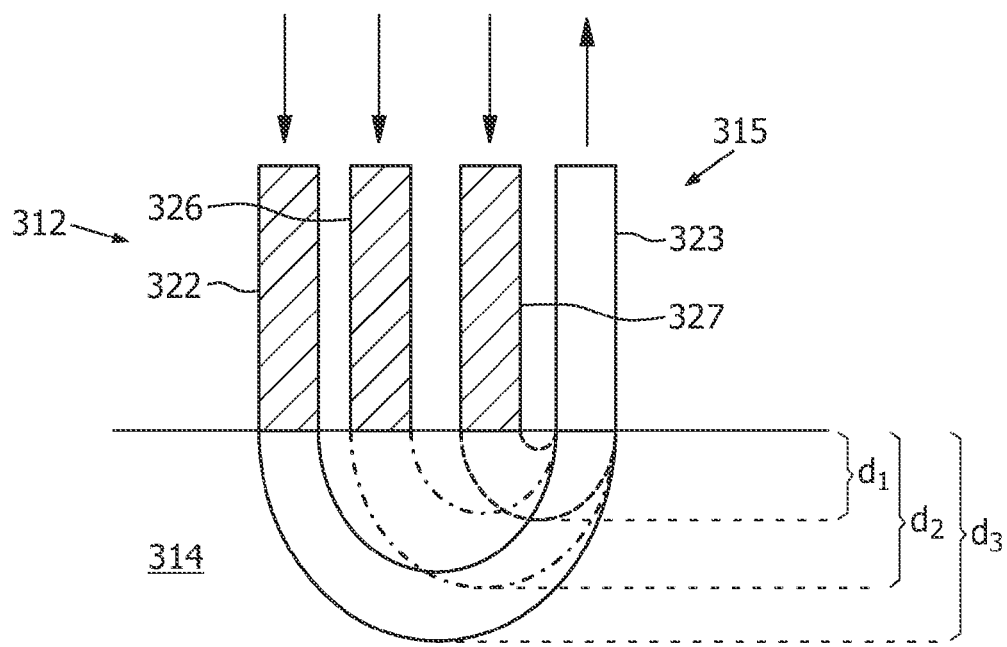
Figure 6:
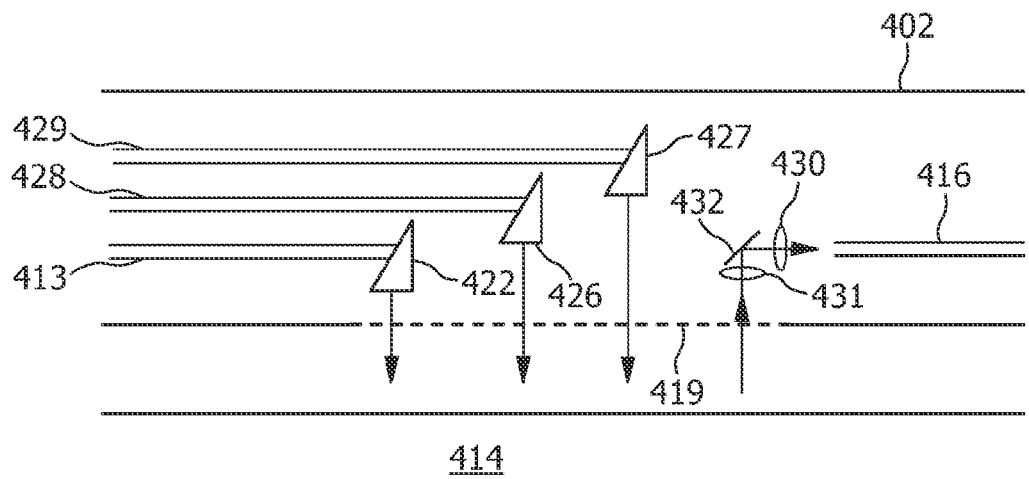
Figure 7:
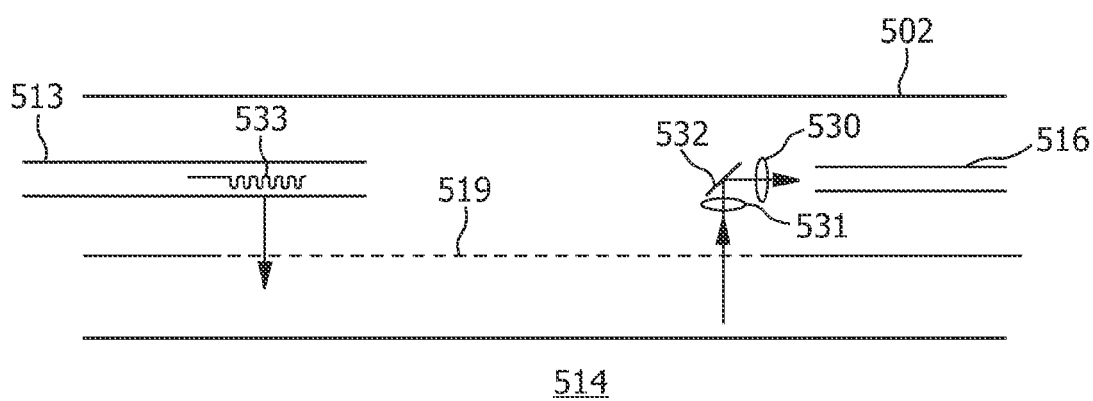
Figure 8:
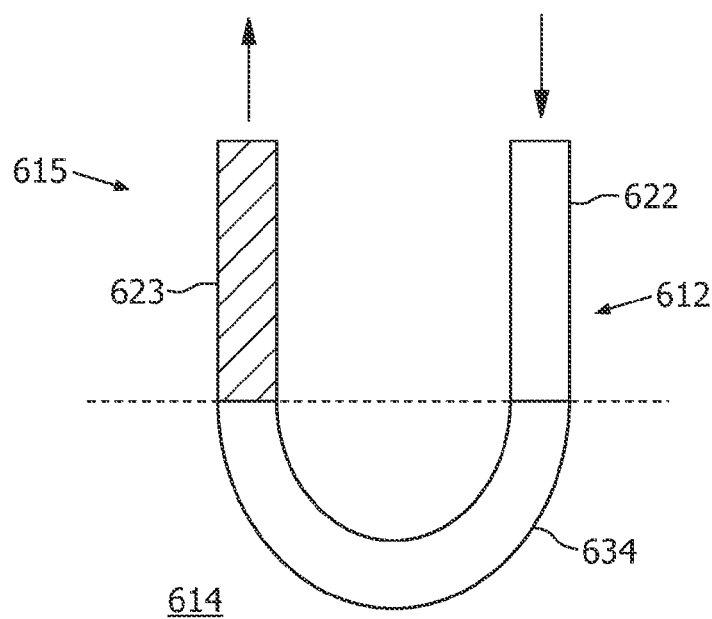
Figure 9:
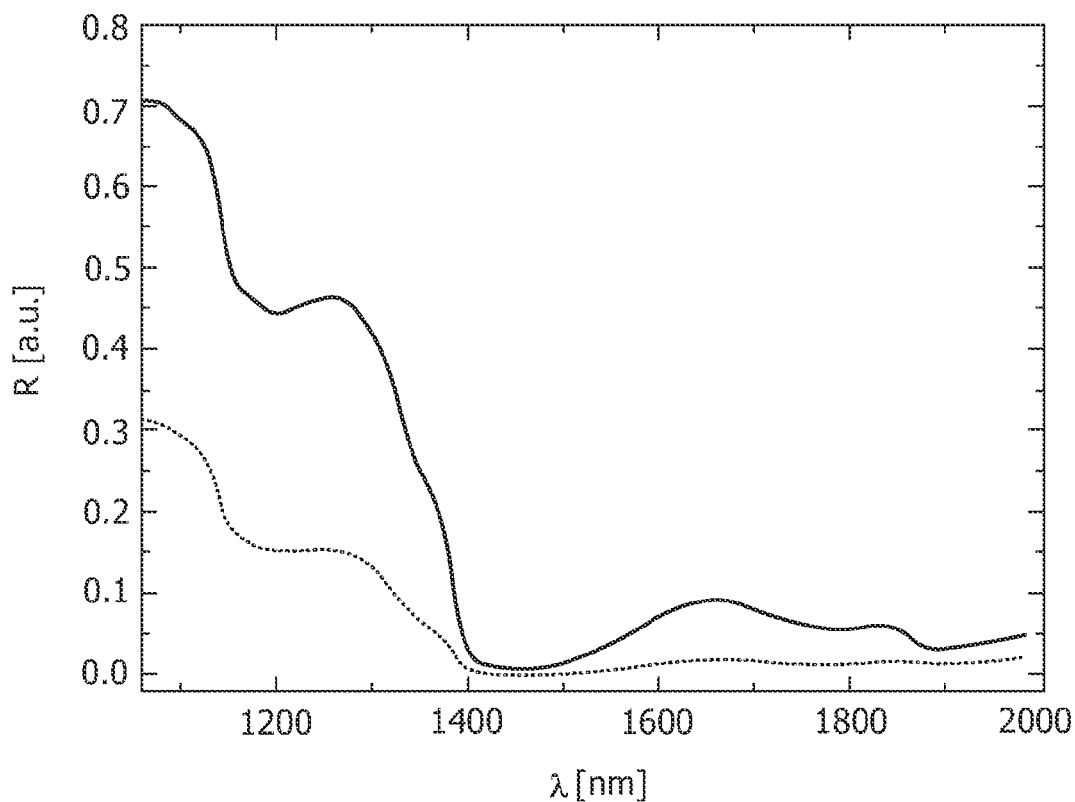
Figure 10:
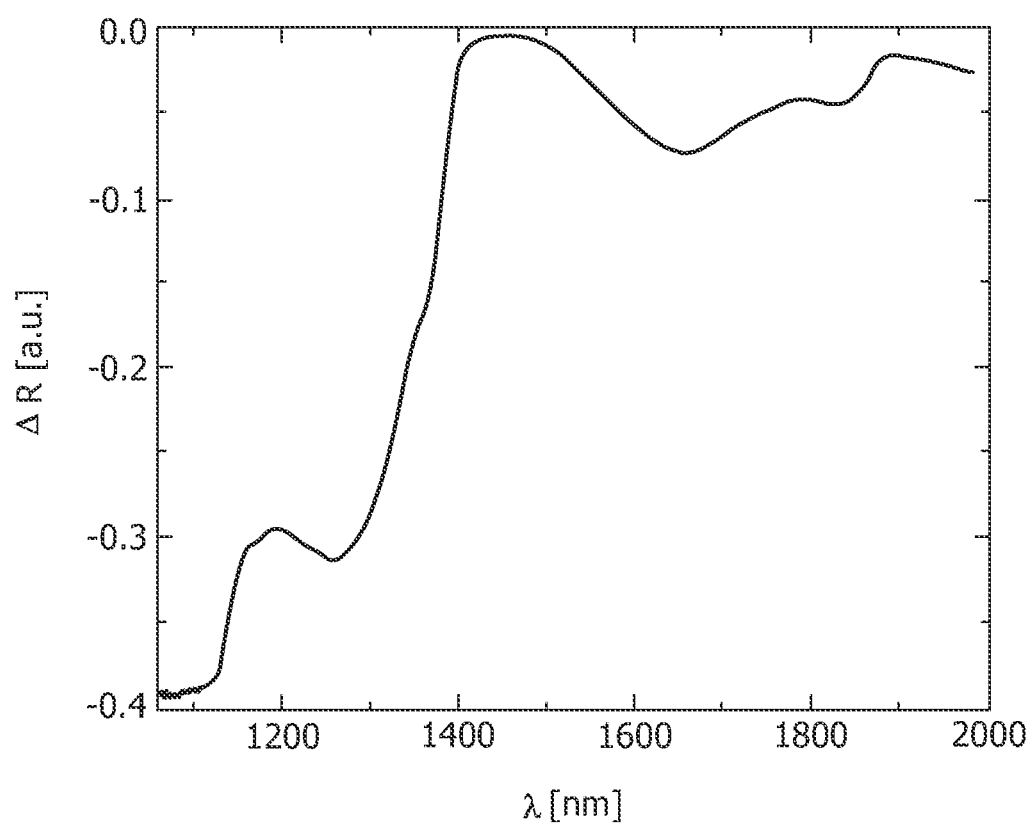
Figure 11:
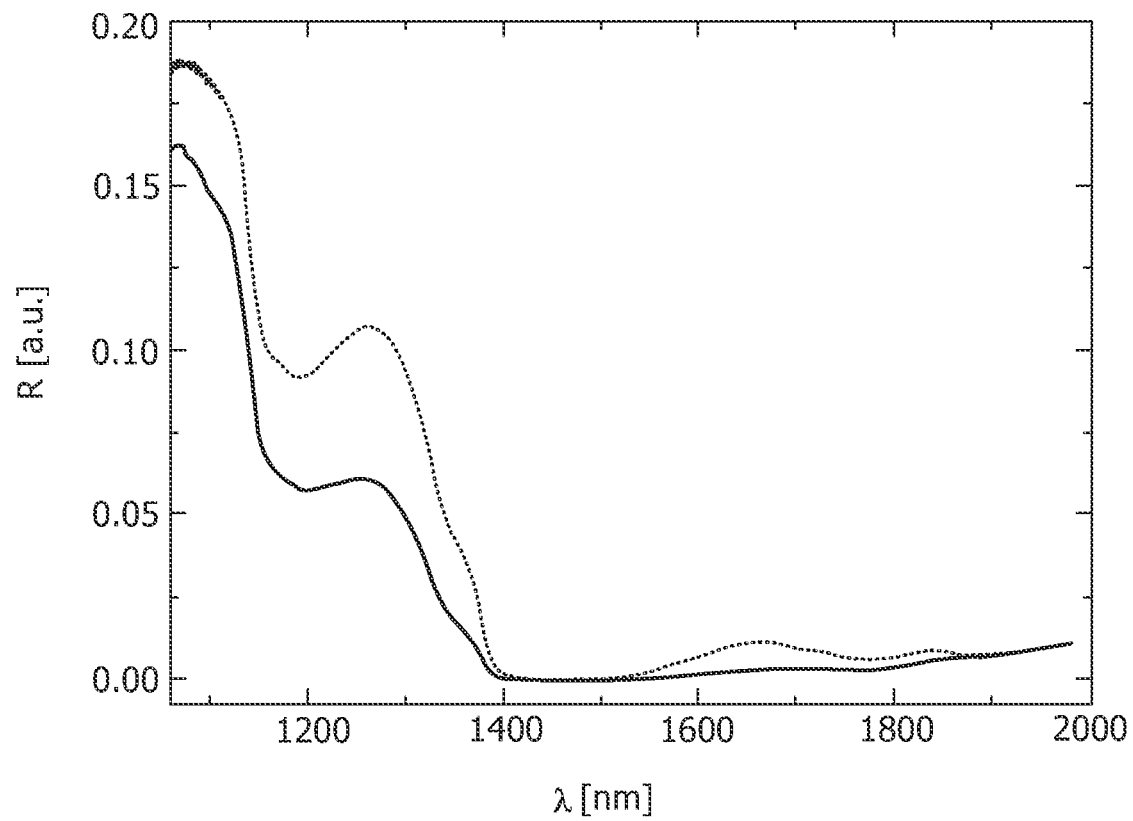
Figure 12:
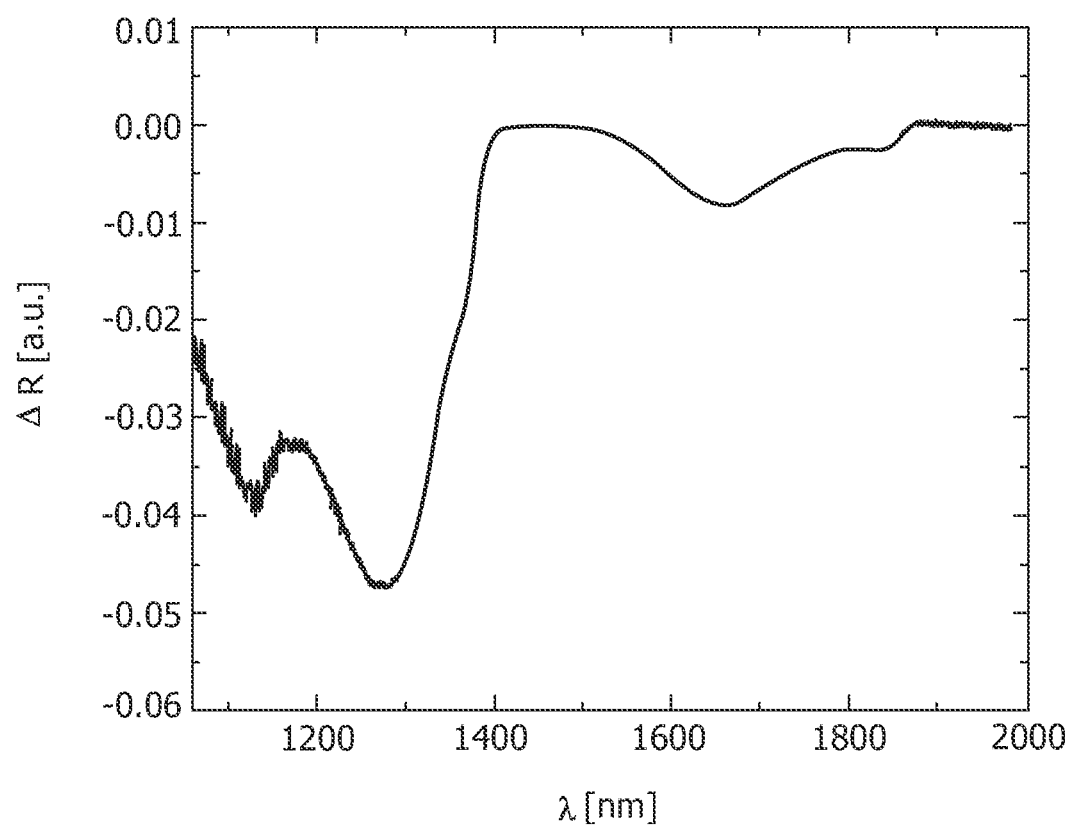
Figure 13:
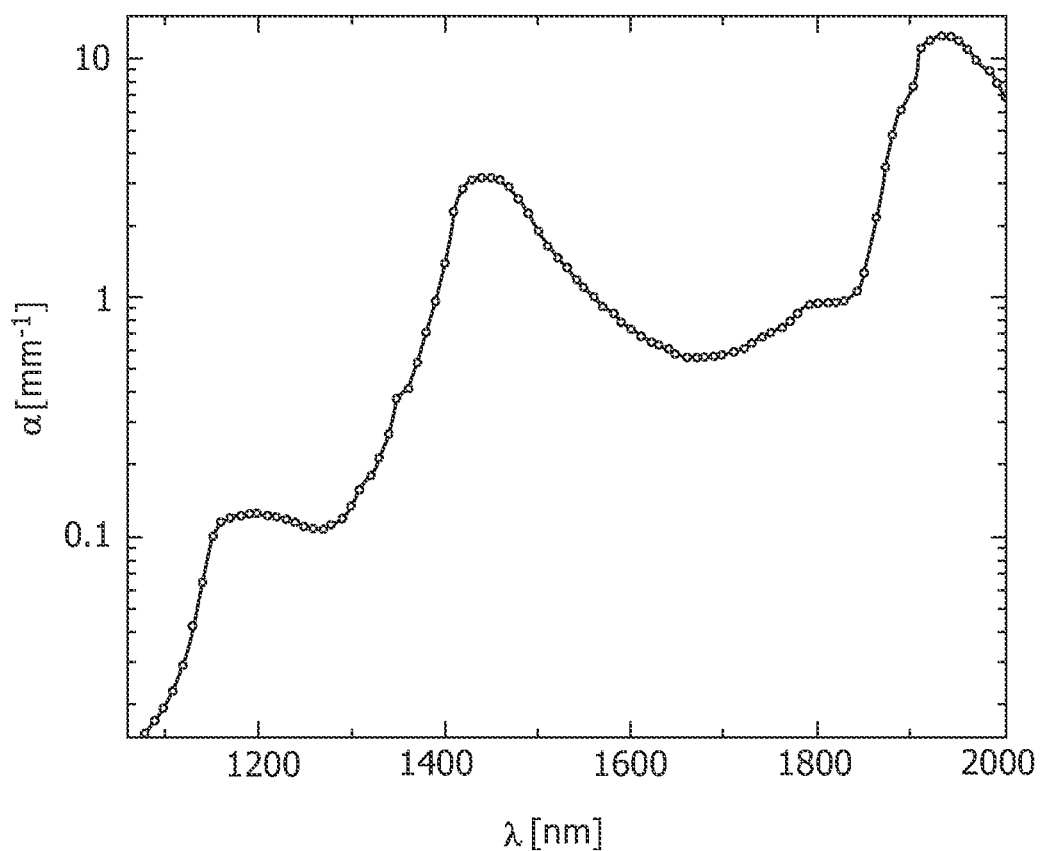
Figure 14:
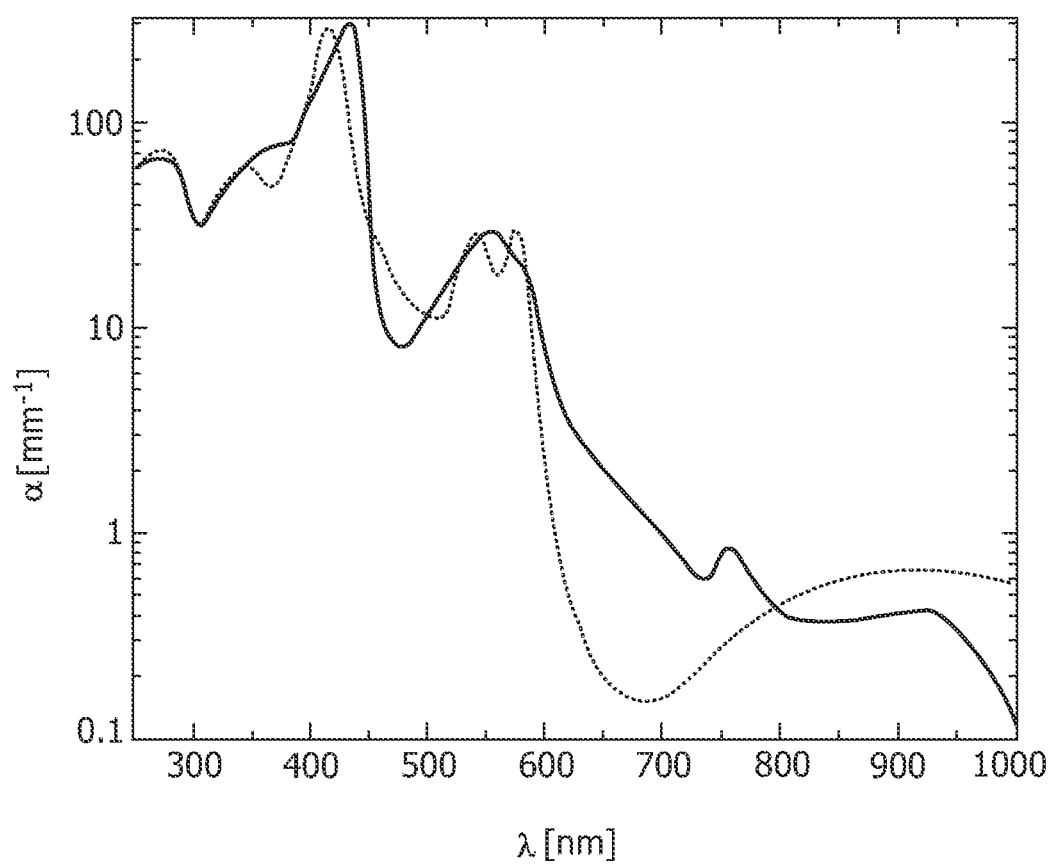
Figure 15:
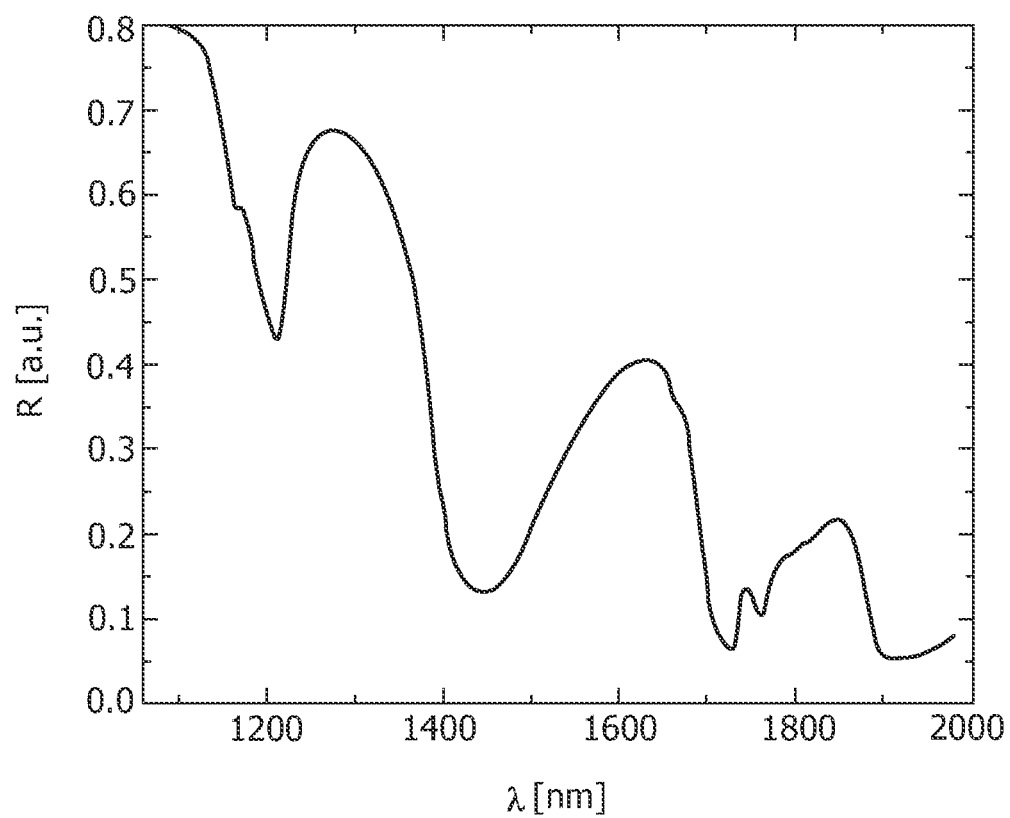
Figure 16:
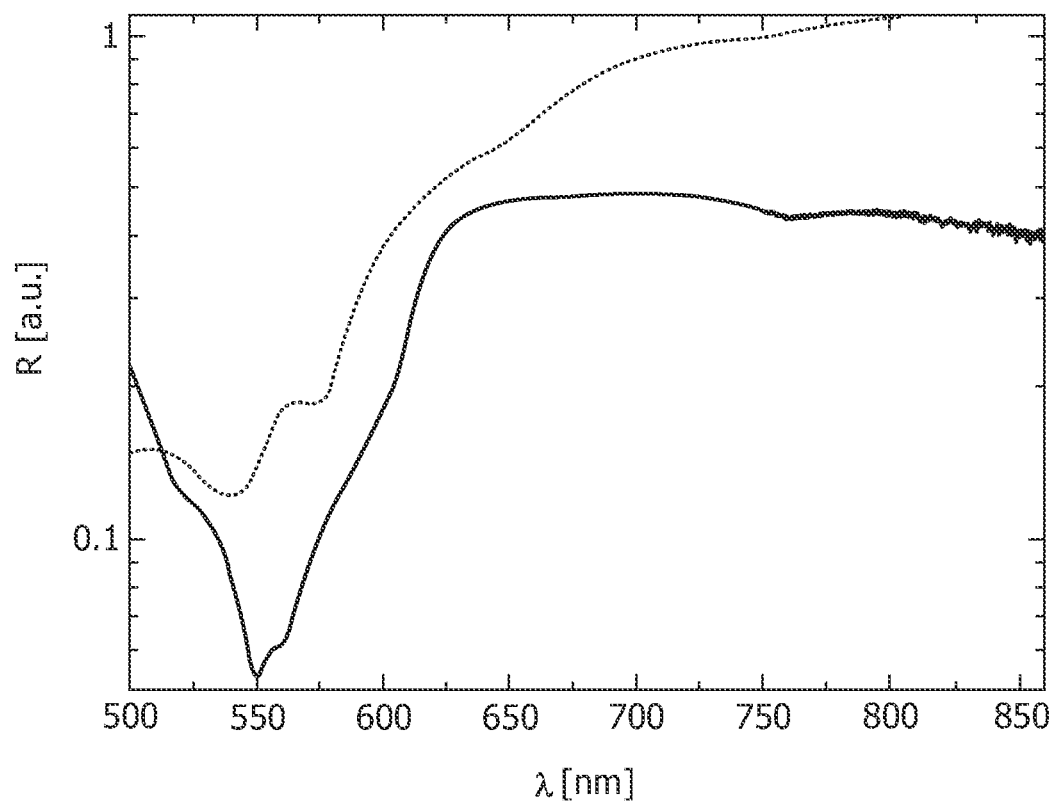
Figure 17:
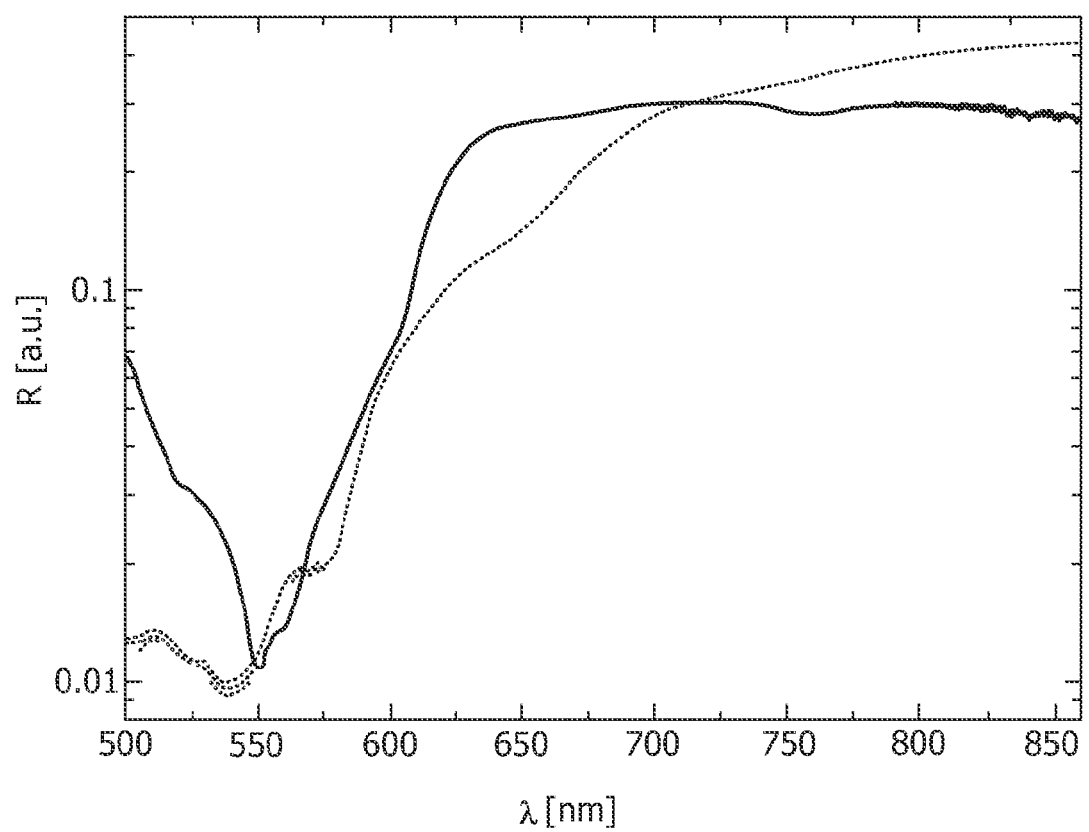
Figure 18:
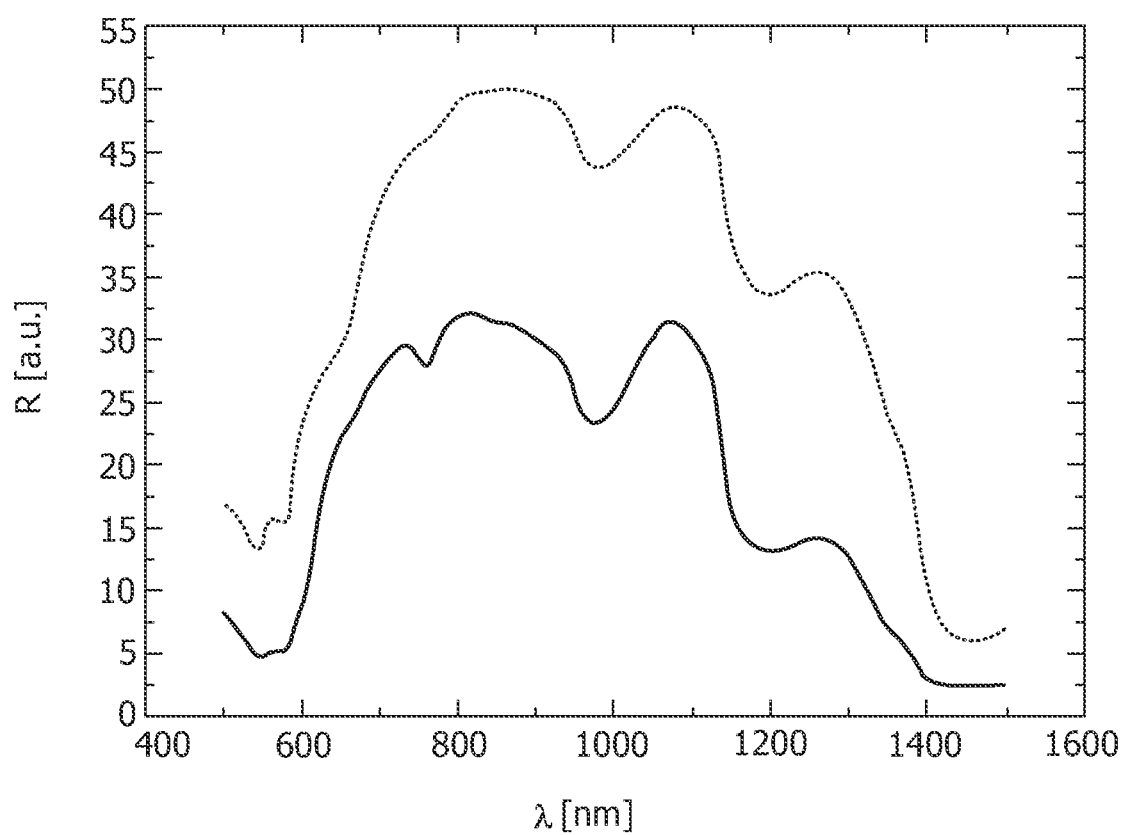

The invention will in the following be described with reference to following figures, wherein FIG. 1 is a schematic view of a laser ablation apparatus according to the invention, FIG. 2 is a schematic view of an end portion of a cardiac ablation catheter of the laser ablation apparatus, FIG. 3 is a schematic view of an apparatus for depth-resolved measurements of properties of tissue inserted into a cardiac ablation catheter according to the invention, FIG. 4 is a schematic view of an arrangement of illumination means and collector means of the apparatus for depth-resolved measurements of properties of tissue according to the invention, FIG. 5 is a schematic view of another arrangement of illumination means and collector means of an apparatus for depth-resolved measurements of properties of tissue according to the invention, FIG. 6 is another schematic view of the arrangement of illumination means and collector means of FIG. 5, FIG. 7 is a schematic view of a further arrangement of illumination means and collector means of an apparatus for depth-resolved measurements of properties of tissue according to the invention inserted into a catheter, FIG. 8 is a schematic view of a further arrangement of illumination means and collector means of an apparatus for depth-resolved measurements of properties of tissue according to the invention, FIG. 9 shows diffuse reflectance spectra of normal and ablated heart tissue, FIG. 10 shows a difference spectrum of diffuse reflectance spectra of normal and ablated heart tissue, FIG. 11 shows other diffuse reflectance spectra of normal and ablated heart tissue, FIG. 12 shows a further difference spectrum of diffuse reflectance spectra of normal and ablated heart tissue, FIG. 13 shows a water absorption spectrum, FIG. 14 shows an absorption spectrum of oxy- and deoxy-hemoglobin, FIG. 15 shows a diffuse reflectance spectrum of cardiac tissue containing fat, FIG. 16 shows further diffuse reflectance spectra of normal and ablated heart tissue, FIG. 17 shows further diffuse reflectance spectra of normal and ablated heart tissue, and FIG. 18 shows VIS/NIR reflectance spectra of normal and ablated heart tissue.

FIG. 1 is a schematic view of a laser ablation apparatus 1. The laser apparatus 1 comprises a cardiac ablation catheter 2 which has been introduced into a blood vessel of a human heart 3. The cardiac ablation catheter is connected to an operational device 4 which includes a measuring light source 5, an ablation light source 6 and a detector 7 for detecting light of the measuring light source 5 which has been directed to the tissue of the human heart 3 and which has not been absorbed by the tissue, but e.g. reflected and/or scattered.

The laser ablation apparatus 1 further comprises a determination means 8, for example a computer, to determine properties of the tissue in different depths from the light detected by the detector 7. The laser ablation apparatus 1 is controlled by a control unit 9, i.e. a control computer, which controls the operational device 4 and the determination means 8.

An end portion 10 of the cardiac ablation catheter 2, which has been introduced into a blood vessel 11 of the human heart 3, is schematically shown in more detail in FIG. 2. An illumination means 12 is located within the cardiac ablation catheter 2. The illumination means is connected to the measuring light source 5 via an optical fiber 13. The illumination means 12 comprises preferentially microprisms (not shown in FIG. 2) to direct the light which has been transmitted from the measuring light source 5 to the illumination means 12 via the optical fiber 13 towards the tissue, which has to be examined, i.e. towards the inner wall of the blood vessel 11. The light emanating from the illumination means 12 penetrates the tissue 14 and is partially absorbed, scattered and/or reflected. Light, which has not been absorbed, is collected by a collector means 15. The collector means 15 comprises preferentially micromirrors and microlenses to collect the light and couple it into an optical fiber 16. The optical fiber 16 transmits the collected light to the detector 7 in the operational device 4. The detector 7 generates detection signals depending on the collected light, and the detection signals are transferred to the determination means 8 which determines properties of the tissue 14 from the detection signals, i.e. the determination means 8 determines properties of the tissue 14 from the collected light, i.e. from the light signals.

In addition, an ablation means 17 is inserted into the cardiac ablation catheter 2 from which light for ablation of tissue 14 emanates. The ablation means 17 is connected to the ablation light source 6 via an optical fiber 18.

By using this laser ablation apparatus 1 the properties of the tissue 14 can be examined during an ablation procedure, and the ablation procedure can be controlled depending on the determined properties of the tissue 14 by the control unit 9.

For example, the control unit 9 can control the laser ablation apparatus 1 such that the determination means 8 or a processor receives continuously or periodically detection signals, e.g., tissue spectra, from the detector 7 in a feedback loop. The determination means 8 or the processor detect changes in the detection signal, e.g., in the tissue spectra, over time, and under certain ablation conditions (i.e., power setting, modulation, etc.). The control unit 9 can control the laser ablation apparatus such that these conditions are varied according to the status of the ablated tissue, which has been determined by the determination means 8 or the processor. The control by the control unit 9 is preferentially an automatic control, but the laser ablation apparatus can also comprise means for indicating that a change has been detected and means for manually changing the ablation conditions in accordance with the indicated changes.

An example is the prevention of surface over-heating (which causes charring): The illumination means can comprise a VIS-(visible) and/or NIR (near-infrared) light source to probe surface/superficial tissue. Spectra that indicate detrimental changes in the tissue optical characteristics could trigger the power and/or modulation settings to be adjusted, for example, the power can be reduced, to prevent further detriment.

Another example is the prevention of damage to healthy tissue layers, e.g., the epicardium. In this case, changes observed in tissue spectra, probing at different depths, are used to determine when to stop applying energy to the tissue.

The cardiac ablation catheter 2 comprises an optical window 19 (dashed line in FIG. 2) which is transparent for the wavelengths of the measuring light source 5 and the ablation light source 6. The optical window 19 is preferentially coated with an organic substance to prevent agglomeration of particles, e.g. bloodcells, on the optical window 19.

A part of the laser ablation apparatus 1 is an apparatus 20 for depth-resolved measurements of properties of tissue which can be used separately from the laser ablation apparatus 1 and which is schematically shown as an independent apparatus in FIG. 3.

The apparatus 20 for depth-revolved measurements of properties of tissue comprises a measuring light source 105 which is connected to an illumination means 112 via an optical fiber 113 in order to transmit light generated by the measuring light source 105 to the illumination means 112 via the optical fiber 113. The illumination means 112 is arranged such that the light, which emanates from the illumination means 112, penetrates the tissue 114 and is partially absorbed, scattered and/or reflected. The light which has not been absorbed is collected by a collector means 115 which is connected to a detector 107 via an optical fiber 116. The light collected by the collector means 115 is transferred to the detector 107 via the optical fiber 116, and the detector 107 converts the collected light into detection signals. The detections signals are transferred to determination means 108, which determines properties of the tissue in different depths from the detection signals, i.e. properties of the tissue in different depths are determined from the collected lights.

The examination process is controlled by the control unit 109, e.g. a control computer, which is connected to the measuring light source 105, the detector 107 and the determination means 108.

The illumination means 112 and the collector means 115 are located in a casing 121 for advancing in a hollow object, e.g. a catheter, comprising an optical window 119 (dashed line in FIG. 3). The optical window 119 is preferentially coated with an organic substance to prevent agglomeration of particles on the optical window 119. The coating and the optical window 119 are transparent for the light of the measuring light source 105.

In FIG. 3 the casing 121 is located within a hollow object, for example, a human heart, wherein only one inner wall of the hollow object is shown.

In the following the arrangement of illumination means and collector means is described in more detail in order to explain the depth-resolved measurement of tissue properties according to the invention.

In FIG. 4 illumination means 212 comprising one illuminator 222 and collector means 215 comprising several collectors 223, 224, 225 are schematically shown. The collectors 223, 224, 225 are preferentially located equidistantly to each other or at the distances on a logarithmic scale. The illuminator 222 is e.g. a microprism which is arranged such that it directs light from a measuring light source towards the tissue 214, which has to be examined. Microprisms are for example known in the field of fiber optical communication applications, particularly in optical switches. The light penetrates the tissue 214 and is partially absorbed, scattered and/or reflected. The light, which has not been absorbed by the tissue 214, is collected by the collectors 223, 224, 225. The light, which is collected by the collector 225 having the smallest distance to the illuminator 222 has a penetration depth $d_1$, which is smaller than the penetration depths $d_2$, $d_3$ of light collected by the other collectors 223, 224. As can be seen in FIG. 4, the penetration depths $d_1$, $d_2$, $d_3$ increase with increasing distance of the collectors 223, 224, 225 to the illuminator 222. Each collector 223, 224, 225 comprises preferentially microlenses, micromirrors or microprisms to collect the light and optical fibers to transfer the collected light to the detector. The detector converts the collected light into detection signals, i.e. light signals are converted into detection signals, and the detections signals are transferred to the determination means. Since for each detection signal the distance of the collector 223, 224, 225, which has collected the corresponding light signal, to the illuminator 222 is known and since the relation between these distances and the penetration depths are also known, for instance, due to a calibration procedure, the properties of the tissue 214 in different depths can be determined from the detection signals.

Preferred methods of calibrating the fiber-to-fiber distance versus penetration depth are either numerical, such as finite element, or by Monte Carlo simulation, or analytical by use of the diffusion approximation. Preferentially, the optical properties of different layers of the object, e.g., different cardiac tissue layers, are measured, under different conditions, using, e.g., absorption spectrometer with integrating spheres. These data are processed using preferentially the inverse adding-doubling method, yielding absorption and scattering coefficients.

Then, using, e.g., a Monte Carlo-based simulation of photon propagation in tissue, a database of average penetration depth corresponding to different fiber-to-fiber distances can be constructed. Alternatively, other numerical methods or analytical methods based on the diffusion approximation can be used for this purpose.

Following calibration, actual measurements are conducted, where preferentially optical spectra are acquired at different fiber-to-fiber separations. Knowing the relationship between fiber-to-fiber distance and penetration depth, acquired spectra can be related to specific depths within the tissue. In a subsequent measurement, an observable change in the spectra indicates changes to the tissue. If the change in the spectra is very small, multivariate analysis (see "*Multivariate Calibration*", H. Martens, T. Naes, John Wiley & Sons; 1 edition (Jul. 28, 1992)) can be used.

The light of the measuring light source is preferentially near-infrared light comprising either one wavelength or a broadband near-infrared spectrum. The detector is preferentially adapted such that the light collected by the different collectors can be detected simultaneously or sequentially in time.

It is further preferred that the light of the measuring light source and/or the ablation light source comprises a) a VIS/NIR spectrum, in particular ranging from 350-2000 nm, and/or b) wavelengths which correspond to absorption bands of heme-containing proteins, water and proteins, and/or c) wavelengths of 414 nm, 434 nm, 542 nm, 556 nm, 576 nm, 758 nm, 914 nm, 1200 nm, 1439 nm, 1932 nm, and/or d) wavelengths between about 1600 and 1900 nm, in particular between 1600 and 1900 nm.

In the following, some spectra will be shown, which can be detected by the detector 7 and which show changes at special wavelengths or wavelengths ranges, from which properties of the tissue and changes of the properties of the tissue can be determined.

FIG. 9 shows diffuse reflectance spectra R ($\lambda$) of normal (dashed line) and ablated (solid line) heart tissue measured with NIR light with approximately 100 microns separation between the illumination means and the collector means. The clear difference in intensity around spectral bands of water, i.e., around 1200 and 1439 nm is visible. Therefore, from these spectra the water content and the change of the water content in the object, i.e., in this embodiment, in the tissue, can be determined. Since these spectra can be detected depth-resolved, in particular, the absorption and the water content can be determined in different depths.

The NIR spectra shown in FIGS. 9-12, and 15 were acquired using an extended InGaAs photodetector.

FIG. 10 shows a difference spectrum $\Delta R$ ($\lambda$) of diffuse reflectance spectra of normal and ablated heart tissue measured with NIR light with approximately 100 microns separation between the illumination means and the collector means, a clear difference and intensity around spectral bands of water, i.e., around 1200 and 1439 nm is visible. An increase in reflection of the ablated tissue (negative values in the difference spectrum between the reflection of the normal and ablated tissue) indicates a decrease of water absorption at these spectral bands and thus a decrease of water content in the ablated tissue.

FIG. 11 shows diffuse reflectance spectra R ($\lambda$) of normal (solid line) and ablated (dashed line) heart tissue measured with NIR light with approximately 1000 microns separation between the illumination means and the collector means. A clear difference in intensity around spectral bands of water, i.e., around 1200 and 1439 nm is visible. This difference is shown separately in FIG. 12.

FIG. 12 shows a difference spectrum of the diffuse reflectance spectra of normal and ablated heart tissue measured with NIR light with approximately 1000 microns separation between the illumination means and the collector means. A clear difference in intensity around spectral bands of water is visible. This indicates a change in water content between the normal and ablated tissue.

Since the spectra shown in FIGS. 9 and 10 have been measured with another distance between the illumination means and the collector means than the spectra shown in FIGS. 11 and 12, from these spectra properties of the object, which is in this embodiment tissue, can be determined in different depths. In this embodiment, in particular, the absorption and the water content in different depths can be determined.

FIG. 15 shows a diffuse reflectance spectrum R ($\lambda$) of cardiac tissue containing fat measured with NIR light with 100 microns separation between the illumination means and the collector means.

From the spectra shown in the FIGS. 16 to 18 the contents of and the change in heme-containing proteins and water can be determined.

FIG. 16 shows diffuse reflectance spectra R ($\lambda$) of normal (solid line) and ablated (dashed line) heart tissue measured with VIS/NIR light with approximately 100 microns separation between the illumination means and the collector means.

A clear difference in intensity around the spectral bands of heme-containing proteins, i.e., around 542, 556, 576, and 758 nm is visible.

FIG. 17 shows diffuse reflectance spectra R (λ) of normal (solid line) and ablated (dashed line) heart tissue measured with VIS/NIR light with approximately 500 microns separation between the illumination means and the collector means. A clear difference in intensity around the spectral bands of heme-containing proteins, i.e., around 542, 556, 576, and 758 nm is visible.

FIG. 18 shows VIS/NIR reflectance spectra of normal (solid line) and ablated (dashed line) bulk (i.e., not depth-resolved) heart tissue as measured using an absorption spectrophotometer with an integrating sphere. Around the heme-containing-protein absorption and the water bands differences between the spectra can be observed.

In order to determine the relations between detected spectra and further object properties, known spectra of elements of the object can be used. These spectra are preferentially used to determine these relations before the actual measurement and to store these relations in the determination unit such that the determination unit can automatically determine the properties of the object in different depths from spectra which have been measured with different distances between the illumination means and the collector means. Such known spectra of elements of human tissue are shown in FIGS. 13 and 14.

FIG. 13 shows a water absorption spectrum a (λ) according to D. J. Segelstein, "The complex reflective index of water", University of Missouri-Kansas City (1981).

FIG. 14 shows an absorption spectrum a (λ) of oxy- (dashed line) and deoxyhemoglobin (solid line) at a concentration of 150 g/l according to W. B. Grather, Med. Res. Council Labs, Holly Hill, London and N. Kollias, Wellman Laboratories, Harvard Medical School, Boston. The change in the spectral bands around Hb absorption, e.g., at 542, 556, 576, and 758 nm is expected upon the tissue ablation. Changes around these spectral bands in other heme-containing proteins, such as myoglobin or cytochrome, are also expected to occur in the ablated heart tissue.

Preferentially, before the actual determination of properties of the object, i.e. the tissue, the apparatus for depth-resolved measurements of properties of tissue is calibrated to determine the relations between the collected light, i.e., the detected signals, in particular, the detected spectra, and the properties of the tissue, for example, the content of certain elements in the tissue, by using measured or known spectra of known elements, which can be present in the tissue.

In FIGS. 4, 5 and 8 the illumination means and collector means are shown with no or a small distance to the tissue. But the invention is not limited to this case. The apparatus for depth-resolved measurements of properties of tissue can also be used, if the distance of the illumination means and/or the collector means to the tissue is larger.

FIG. 5 shows schematically another arrangement of the illumination means 312 and collector means 315 according to the invention. The illumination means 312 comprises several illuminators 322, 326, 327, which have different distances to the collector means 315. The collector means 315 comprises one collector 323. The illuminators 322, 326, 227 are connected to a measuring light source via optical fibers. The illuminators 322, 326, 327 are arranged such that light, which emanates from the illuminators 322, 326, 327, penetrates the tissue 314 which partially absorbs, scatters and/or reflects the light. The light, which has not been absorbed, is collected by the collector 323, which is connected to a detector via an optical fiber. The detector converts the collected light into detection signals, i.e. the detector converts light signals into detection signals, and these detection signals are transferred to determination means.

Similar to the arrangement of FIG. 4, also in FIG. 5 the penetration depths $d_1$, $d_2$, $d_3$ increase with increasing distance of the illuminators 322, 326, 327 to the collector 323. The apparatus for depth-resolved measurements of properties of tissue according to the invention, which uses this arrangement, is adapted to distinguish light, which emanates from different illuminators 322, 326, 327. If the light of the measuring light source is a broadband near-infrared spectrum or if the light of the measuring light source comprises only one wavelength, the illuminators 322, 326, 327 illuminate the tissue 314 sequentially in time in order to distinguish light emanated from different illuminators 322, 326, 327. In order to distinguish light emanated from different illuminators 322, 326, 327 also different wavelengths can be used, wherein each illuminator comprises one single wavelength, which is different from the wavelength of the other illuminators. Alternatively, each illuminator 322, 326, 327 can emanate light comprising several wavelengths, wherein light of different illuminators 322, 326, 327 comprise different wavelengths in order to distinguish light emanated from different illuminators 322, 326, 327.

In order to provide the illuminators 322, 326, 327 with light having different wavelengths, the apparatus for depth-resolved measurements of properties of tissue can comprise several measuring light sources, wherein different measuring light sources emit light having different wavelengths. Each illuminator 322, 326, 327 can be connected to one of these measuring light sources via an optical fiber. Alternatively, only one measuring light source or several measuring light sources comprising overlapping light spectra can be used, wherein the light spectrum of the one measuring light source or the light spectra of the several measuring light sources comprising overlapping light spectra is spatially divided into different wavelengths by e.g. a grating or a prism. The light, which is spatially divided into different wavelengths, is coupled to optical fibers such that the optical fibers transfer the light to the illuminators 322, 326, 327 such that light of different illuminators 322, 326, 327 comprise different wavelengths.

The determination means receives detection signals from the detector, wherein, because for each detection signal the distance of the illuminator 322, 326, 327, which has emanated the corresponding light, to the collector 323, e.g. since the wavelength or the wavelengths of the corresponding light is known, and since the relation between theses distances and the penetration depths is also known, e.g. by calibration, the determination means determines, as explained above, the properties of the tissue in different depths from the detection signals, i.e. from the collected light. If different wavelengths are used to distinguish light collected by different collectors, the light collected by different collectors can be collected simultaneously.

FIG. 6 shows the arrangement of FIG. 5 within a catheter 402. Light from a measurement light source is transferred to illuminators 422, 426, 427. The illuminators comprise preferentially microprisms. These microprisms direct the light towards the tissue 414. The light, which has not been absorbed by the tissue 414, is collected by the collector comprising preferentially microlenses 430, 431 and a micro mirror 432, which collect the light and couple it into an optical fiber 416, which is connected to a detector.

FIG. 7 shows schematically another arrangement of illumination means and collector means according to the invention within a catheter 502. The illumination means comprises a grating coupler 533 which couples light, which has been transferred from a measurement light source via an optical fiber 513 to the grating coupler 533, from the optical fiber 513 into the tissue 514. The light, which has not been absorbed by the tissue 514, is collected by collector means which comprise microlenses 530, 531 and a micromirror 532 to collect the light and couple it into the optical fiber 516 which is connected to a detector. The catheter 502 comprises an optical window 519 which is transparent for the light of the measuring light source. The optical window 119 is preferentially coated with a substance, in particular an organic substance, to prevent agglomeration of particular on the optical window 519.

The illumination means and the collector means of the apparatus for depth-resolved measurements of properties of tissue according to the invention can be adapted such that they are moveable relatively to each other in order to collect light with different distances between the collector means and the illumination means. Since, as shown in FIGS. 4 and 5, different distances between the collector means and the illumination means correspond to different penetration lengths of the collected light, i.e. of the light signals, the light can be collected depth-resolved by an apparatus comprising illumination means and collector means which are moveable relative to each other. This depth-resolved collected light is preferentially used by a detector and a determination means in order to determine properties of the tissue in different depths from this depth-resolved collected light, as explained above.

In the arrangement according to FIG. 8, the illumination means 612 comprises one illuminator 622 and the collector means 615 comprises one collector 623. Light having different wavelengths is transferred from a measuring light source via an optical fiber to the illuminator 622, which comprises preferentially a microprism to couple the light into the tissue 614. The light, which has not been absorbed by the tissue 614 and which has traveled along the light pass 634 through the tissue 614, is collected by the collector 623. The collector 623 collects the light and couples it into an optical fiber, which transfers the light to a detector. In this arrangement only one illuminator 612 and one collector 623 is used. Different wavelengths comprise different penetration lengths depending on the optical properties of the tissues. Therefore, the detector detects a light spectrum and converts the light spectrum into a spectrum of detection signals which is transferred to a determination means. Since the relation between the wavelengths and the penetration depths is known, e.g. by calibration, the determination means is able to assign to each wavelength a penetration depth, and since for each wavelength a detection signal has been transferred to the determination means, the determination means can determine properties of the tissue in different depths from the detection signals, as explained above, i.e. from the collected light.

As illumination means and collector means, i.e. as illuminator and collector, the apparatus for depth-resolved measurements of properties of tissue according to the invention can comprise any component, which is able to couple the light from an optical fiber into the tissue and to couple the light, which has not been absorbed by the tissue, from the tissue into an optical fiber, respectively. Instead of optical fibers also planar waveguides with transmission characteristics optimized for the selected wavelengths can be used. Furthermore, the optical fiber or planar waveguides can comprise bandpass or cut-off filters. Alternatively, the illumination means can only comprise one or several optical fibers and/or the collector means can also comprise only one or several optical fibers, without comprising further optical elements like prisms, lenses or mirrors. In this case, the tissue is illuminated with light emanating directly from the optical fibers of the illumination means, and the light, which has not been adsorbed by the tissue, is collected directly by the optical fibers of the collector means. Additionally, polarization-sensitive optical components, such as e.g., a polarizer, can be used to illuminate the sample and/or detect optical signals with different polarizations. This can provide additional information on properties of the tissue, in particular on the ablated tissue status.

The ablation apparatus according to invention comprising the apparatus for depth-resolved measurements of properties of tissue can be used to control temperature-induced tissue changes produced during cardiac ablation.

It is known e.g. from "Comparison of thermal tissue effects induced by contact applications of fiber guided laser systems", Janda et al., Lasers in surgery and medicine, 33:93-101 (2003) and "Optical properties of normal, diseased, and laser photocoagulated myocardium at the Nd:YAG wavelength", Splinter et al., Lasers in surgery and medicine, 11: 117-124 (1991) that heating up tissue during laser-induced ablation will result in tissue changes. They include (i) changes in cell structure, (ii) degradation of tissue components, such as e.g., hemoglobin, myoglobin, cellular enzymes and other proteins (collagen), and (iii) water loss (see FIGS. 9-12, 16-18).

Changes in cell structure typically result in a change, e.g., an increase of light scattering, and the denaturing of components leads into changes in their spectra. Thus, as it is known from e.g. "Birefringence characterization of biological tissue by use of optical coherence tomography", Everett et al., Optics Letters, 23/3:228-230 (1998) and "Dynamics of tissue optics during laser heating of turbid media", Lin et al., Applied Optics, 35/19:3413-3420 (1996), spectroscopic tools can provide information on temperature-induced tissue changes. This information could be used as a feedback mechanism during laser-induced cardiac ablation to control the process, making it more efficient and preventing high-temperature induced tissue carbonization/rupturing. Vibrational spectroscopy, including Raman spectroscopy, near- and mid-infrared spectroscopy, have proven themselves as highly sensitive and specific tools for studying molecular composition and its changes in different types of sample, including both in-vivo and in-vitro samples. Thus, the detector or the determination unit of the apparatus for depth-resolved measurements of properties of an object comprises preferentially a spectroscope to measure the changes in the spectra of light which has been collected by the collector means.

Current tools applied for cardiac ablation do not allow for such an inspection of temperature-induced changes of the tissue which leads to a limitation of the reliability of the ablation procedure and which can lead to tissue overheating, which could result in undesirable tissue carbonization or vaporization, perforation or rupturing in known ablation procedures. In contrast, the ablation apparatus according to the invention allows to determine the properties of the tissue depth-resolved also during an ablation procedure. Thus, temperature-induced tissue changes produced during cardiac ablation can be determined during the ablation procedure, and the ablation procedure can be controlled, e.g. by the control unit 9, depending on the determined temperature-induced tissue changes in order to prevent tissue overheating. Therefore, temperature-induced tissue changes can be controlled in real-time during cardiac ablation.

As mentioned above, by using the laser ablation apparatus according to the invention a depth-resolved control of tissue during an ablation procedure is possible, since it allows for control of temperature-induced changes produced during cardiac ablation, e.g. a more tight regulation of necessary laser power and/or duration of treatment and/or temperature by the control unit is possible due to the invention. This could prevent possible complications and unnecessary tissue damage. Furthermore, this would increase the rate of successful treatments. It could also help to reduce the duration of the treatment because the user may not have to repeat the procedure, since there is a precise control of required parameters and a direct feedback of treatment progress can be determined by the apparatus according to the invention.

The ablation apparatus according to the invention uses preferentially a laser light source as the ablation light source, because a laser-based treatment provides increased depth of penetration, greater control over lesion size and shape, compared with known ablation apparatuses which do not use laser light for the ablation.

The laser light has preferentially wavelengths in the near-infrared since it provides sufficient tissue penetration and can be performed using a relatively simple design of the apparatus. By using such an apparatus according to the invention using near-infrared laser light in a reflection mode, i.e. in a mode, in which light, which is reflected from and/or scattered by the tissue, is collected by the collector means, within a blood vessel of a human heart 3 superficial tissue layers as well as layers as deep as e.g. 3 to 4 mm below the surface can be scanned. That is, for instance, within a human heart the myocardium and the epicardium can be scanned.

The above mentioned U.S. Pat. No. 5,197,470 discloses an instrument which is intended to be used for the detection of diseased tissue portions only. In contrast, the apparatus for depth-resolved measurements of properties of tissue according to the invention can be used to monitor laser-induced changes in the tissue. Furthermore, the instrument disclosed in U.S. Pat. No. 5,197,470 is intended to be used for detection of cholesterol and its esters only. In contrast, the apparatus for depth-resolved measurements of properties of tissue according to the invention preferentially uses wavelengths, which are different to the wavelengths used by the instrument disclosed in U.S. Pat. No. 5,197,470 and which can be used to detect especially water, proteins and heme-containing proteins. Furthermore, in contrast to the apparatus for depth-resolved measurements of properties of tissue according to the invention, the instrument disclosed in U.S. Pat. No. 5,197,470 is used for atherosclerosis treatment only. Furthermore, in contrast to the invention, the document U.S. Pat. No. 5,197,470 does not disclose depth-resolved measurements and the use of depth-resolved measurements during a cardiac ablation procedure.

Although in FIGS. 1 and 2 and in the corresponding description the ablation apparatus is described comprising an ablation light source 6, a measuring light source 5, respective optical fibers 13, 18, and illumination 12 and ablation means 17, the invention is not limited to this arrangement. For instance, the ablation apparatus could also only comprise the ablation light source 6, optical fiber 18 and the ablation means 17, without comprising a separate measuring light source 5, respective optical fibers 13 and the illumination means 12. In this case, the collector means is adapted to collect light, which has been emanated from the ablation means and which has been reflected and/or scattered from the tissue, i.e. the ablation means has the function of the illumination means.

The light signals which have been collected by the collector means and which are transferred to the detector via an optical fiber can be used to determine the properties of the tissue during the ablation procedure, i.e. the ablation apparatus according to the invention allows the monitoring of penetration during the ablation and it allows the user to identify whether the desired lesion depth has been achieved. Thus, the depth-resolved determination of properties of the tissue by using e.g. depth-resolved spectral information can be used to determine when to terminate the ablation procedure. For instance, the control unit or a user can stop the ablation procedure, if the determination unit determines that the diseased tissue has been removed or damaged, or if healthy tissue impends to be damaged. This control of the ablation procedure is particularly important during the production of an ablation lesion spanning the entire thickness of myocardial tissue. In this case, a damage of delicate structures around the epicardium, and possible side effects on other organs in the proximity of the heart has to be prevented.

Apart from laser-assisted ablation the apparatus for depth-resolved measurements of properties of tissue according to the invention can be applied to monitor tissue changes induced by other methods, such as ultrasound, microwave, radio frequency (RF) and cryo ablation.

The apparatus for depth-resolved measurements of properties of tissue according to the invention can be also applied to the measurement of lesions caused by diseases, such as ulcers (e.g. colitis) and scars from previous surgical procedures.

The apparatus for depth-resolved measurements of properties of tissue according to the invention can be also applied to monitor cardiac angiogenesis and revascularization based on changes in tissue perfusion.

Each of the above described apparatuses for depth-resolved measurements of properties of tissue can be used together with the ablation apparatus according to the invention.

The invention is not limited to the detection of light spectra, for example, also light of a single wavelength can be detected to determine properties of an object.

The invention claimed is:

1. An apparatus for depth-resolved measurements of properties of tissue, said apparatus comprising:
   a) an illumination device configured to illuminate the tissue with light;
   b) a collector device configured to collect light which has not been absorbed by the tissue;
   c) a determination device configured to determine properties of the tissue in different depths from the collected light;
   d) a casing, in which at least a part of the illumination device and the collector device are located, for advancing into a hollow object,
   wherein the illumination device and the collector device are configured to collect light depth-resolved, and wherein the determination device is configured to determine depth-resolved properties of the tissue from the light, which has been collected depth-resolved,
   wherein the illumination device comprises different illuminators that are arranged circularly around the collector device and are movable to change a distance between the illumination device and the collector device in order to collect light signals having different penetration lengths.

2. The apparatus according to claim 1, wherein the illumination device and the collector device are configured to collect light signals of the light which has not been absorbed by the tissue, wherein at least some of the light signals have penetrated the tissue up to different penetration depths, and wherein the determination device is configured to determine the properties of the tissue in different depths from the light signals.

3. The apparatus according to claim 2, wherein the illumination device and the collector device are configured to collect light signals of the light which has been directly reflected at the surface of the tissue.

4. The apparatus according to claim 2, wherein the illumination device and the collector device are configured to collect light signals which have entered the tissue at an entering position and which have left the tissue at a leaving position, wherein for at least some of the collected light signals the distance between the entering position and the leaving position is different.

5. The apparatus according to claim 1, wherein the collector device comprises a plurality of collectors and wherein each collector of the plurality of collectors is located at a predetermined distance from a position at which an illuminator of the different illuminators is located and wherein predetermined distances from at least two collectors to the illuminator are different.

6. The apparatus according to claim 1, wherein the determination device is configured to assign to each of the different wavelengths a penetration depth and to determine from light with a wavelength the properties of the tissue at the penetration depth which has been assigned to the respective wavelength.

7. The apparatus according to claim 1, wherein at least one of the illumination device and the collector device comprises at least one of a microprism, a microlens, a micromirror, an optical fiber and a waveguide.

8. The apparatus according to claim 1, wherein the light comprises at least one of:
   a) near-infrared light,
   b) visible light,
   c) wavelengths, which correspond to absorption bands of heme-containing proteins, water and proteins,
   d) wavelengths within a band around 414 nm, 434 nm, 542 nm, 556 nm, 576 nm, 758 nm, 914 nm, 1200 nm and/or 1439 nm, 1932 nm, and
   e) wavelengths between 1600 and 1900 nm.

9. The apparatus according to claim 1, wherein at least one of the illumination device and the collector device comprises one or more polarizing or polarization-sensitive components.

10. The apparatus according to claim 1, wherein the casing is a catheter.

11. The apparatus according to claim 1, wherein the casing comprises an optical window which is transparent at least for a predetermined range of wavelengths or at least for a predetermined wavelength of light with which the tissue is to be illuminated.

12. The apparatus according to claim 11, wherein the optical window is coated with a substance which is configured to prevent agglomeration of particles on the optical window.

13. An ablation apparatus for ablating tissue comprising the apparatus for depth-resolved measurements of properties of tissue according to claim 1.

14. The apparatus of claim 1, wherein the illumination device comprises different illuminators, and wherein light of the different illuminators comprise different wavelengths in order to distinguish light emanated from the different illuminators, and wherein the different illuminators are configured to simultaneously emanate different lights having the different wavelengths.

15. The apparatus of claim 1, wherein the different illuminators are arranged in a ring around the collector device, and wherein a radius of the ring varies with time.

16. The apparatus of claim 1, wherein the different illuminators are arranged in a spiral around the collector device.

17. A method for depth-resolved measurements of properties of issue comprising the acts of:
   a) advancing an illumination device and a collector device of an apparatus for depth-resolved measurements of properties of tissue into a hollow object;
   b) illuminating the tissue with light by the illumination device;
   c) collecting of light, which has not been absorbed by the tissue, by the collector device;
   d) determining properties of the tissue in different depths from the collected light by determination device, wherein the light is collected depth-resolved and wherein depth-resolved properties of the tissue are determined from the light, which has been collected depth-resolved, wherein the illumination device comprises different illuminators that are arranged circularly around the collector device and are movable to change a distance between the illumination device and the collector device in order to collect light signals having different penetration lengths.

18. The method of claim 17, wherein the illumination device comprises different illuminators, and wherein light of the different illuminators comprise different wavelengths in order to distinguish light emanated from the different illuminators, and wherein the different illuminators are configured to simultaneously emanate different lights having the different wavelengths.

19. The method of claim 17, wherein the different illuminators are arranged in a ring around the collector device, and wherein a radius of the ring varies with time.

20. The method of claim 17, wherein the different illuminators are arranged in a spiral around the collector device.

21. An apparatus for depth-resolved measurements of properties of tissue, said apparatus comprising:
   a) an illumination device configured to illuminate the tissue with light;
   b) a collector device configured to collect light which has not been absorbed by the tissue;
   c) a determination device configured to determine properties of the tissue in different depths from the collected light;
   d) a casing, in which at least a part of the illumination device and the collector device are located, for advancing into a hollow object,
   wherein the illumination device and the collector device are configured to collect light depth-resolved, and wherein the determination device is configured to determine depth-resolved properties of the tissue from the light, which has been collected depth-resolved,
   wherein the collector device comprises a plurality of collectors, the plurality of collectors being arranged circularly around the illumination device and being movable to change a distance between the illumination device and the collector device in order to collect light signals having different penetration lengths.

22. The apparatus of claim 21, wherein the plurality of collectors is arranged in a ring around the illumination device, and wherein a radius of the ring varies with time.

23. The apparatus of claim 21, wherein the plurality of collectors is arranged in a spiral around the illumination device.

* * * * *